US010730816B2

(12) United States Patent
Gao et al.

(10) Patent No.: US 10,730,816 B2
(45) Date of Patent: Aug. 4, 2020

(54) METHOD OF SELECTIVELY OXIDIZING LIGNIN

(71) Applicant: Wisconsin Alumni Research Foundation, Madison, WI (US)

(72) Inventors: Ruili Gao, Fitchburg, WI (US); John Ralph, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 16/217,569

(22) Filed: Dec. 12, 2018

(65) Prior Publication Data
US 2019/0177259 A1    Jun. 13, 2019

Related U.S. Application Data

(60) Provisional application No. 62/597,676, filed on Dec. 12, 2017.

(51) Int. Cl.
| | | |
|---|---|---|
| C07C 45/29 | (2006.01) | |
| B01J 27/00 | (2006.01) | |
| B01J 31/02 | (2006.01) | |
| B01J 27/132 | (2006.01) | |
| C07C 41/26 | (2006.01) | |
| B01J 31/20 | (2006.01) | |
| B01J 31/24 | (2006.01) | |
| B01J 31/22 | (2006.01) | |

(52) U.S. Cl.
CPC .......... C07C 45/29 (2013.01); B01J 27/132 (2013.01); B01J 31/0222 (2013.01); C07C 41/26 (2013.01); C07C 45/294 (2013.01); B01J 31/20 (2013.01); B01J 31/2295 (2013.01); B01J 31/2409 (2013.01); B01J 2531/64 (2013.01); C07C 2601/16 (2017.05)

(58) Field of Classification Search
CPC .............................. B01J 27/132; C07C 45/29
See application file for complete search history.

(56) References Cited

U.S. PATENT DOCUMENTS

| | | | | |
|---|---|---|---|---|
| 9,359,391 B2 * | 6/2016 | Stahl | ................... | C07G 1/00 |
| 9,790,249 B2 * | 10/2017 | Beckham | ................ | C07G 1/00 |
| 2017/0029713 A1 * | 2/2017 | Powell | ................. | C10G 3/50 |

OTHER PUBLICATIONS

Zhu et al. An efficient and recyclable catalytic system comprising nanopalladum (0) and a pyridinium salt of iron bis (dicarbollide) for oxidation of substituted benzyl alchohol and lignin. ChemistryOpen, vol. 1, 67-70. (Year: 2012).*
Badalyan et al., Cooperative electrocatalytic alcohol oxidation with electron-proton-transfer mediators. Nature 2016, 535, 406-410.
Badamali et al., Microwave assisted oxidation of a lignin model phenolic monomer using Co(salen)/SBA-15. Catalysis Communications 2009, 10, 1010-1013.
Biannic et al., Efficient cobalt-catalyzed oxidative conversion of lignin models to benzoquinones. Organic Letters 2013, 15, 2730-2733.
Boerjan et al., Lignin biosynthesis. Annual Reviews in Plant Biology 2003, 54, 519-546.
Chen et al., Nucleophilic acyl substitutions of esters with protic nucleophiles mediated by amphoteric, oxotitanium, and vanadyl species. Journal of Organic Chemistry 2005, 70, 1328-1339.
Conesa et al., A microwave approach to the selective synthesis of omega-laurolactam. Green Chemistry 2007, 9, 1109-1113.
Enemark et al., Synthetic analogues and reaction systems relevant to the molybdenum and tungsten oxotransferases. Chemical Reviews 2004, 104, 1175-1200.
Freudenberg et al., Constitution and Biosynthesis of Lignin; Springer-Verlag: Berlin-Heidelberg-New York, 1968.
Garcia et al., A selective, efficient and environmentally friendly method for the oxidative cleavage of glycols. Green Chemistry 2016, 18, 2335-2340.
Hanson et al., C—C or C—O Bond cleavage in a phenolic lignin model compound: selectivity depends on vanadium catalyst. Angewandte Chemie-International Edition 2012, 51, 3410-3413.
Hanson et al., Knocking on wood: base metal complexes as catalysts for selective oxidation of lignin models and extracts. Accounts of Chemical Research 2015, 48, 2037-2048.
Jeyakumar et al., Aerobic oxidation of benzyl alcohols by Mo—VI compounds. Applied Organometallic Chemistry 2006, 20, 840-844.
Jeyakumar et al., Application of molybdenum(VI) dichloride dioxide ($MoO_2Cl_2$) in organic transformations. Journal of Chemical Sciences 2009, 121, 111-123.
Kumar et al., Hierarchical self-assembly of donor-acceptor-substituted butadiene amphiphiles into photoresponsive vesicles and gels. Angewandte Chemie-International Edition 2006, 45, 6317-6321.
Lancefield et al., Isolation of functionalized phenolic monomers through selective oxidation and C—O bond cleavage of the β-O-4 linkages in lignin. Angewandte Chemie (International Edition) 2015, 54, 258-262.
Li et al., Catalytic transformation of lignin for the production of chemicals and fuels. Chemical Reviews 2015, 115, 11559-11624.
Ma et al., Catalytic oxidation of biorefinery lignin to value-added chemicals to support sustainable biofuel production. ChemSusChem 2015, 8, 24-51.
Mottweiler et al., Copper- and vanadium-catalyzed oxidative cleavage of lignin using dioxygen. Chemsuschem 2015, 8, 2106-2113.
Nakatsubo et al., Synthesis of guaiacylglycerol-β-guaiacyl ether. Holzforschung 1975, 29, 165-8.
Quideau et al., Facile large-scale synthesis of coniferyl, sinapyl, and p-coumaryl alcohol. Journal of Agricultural and Food Chemistry 1992, 40, 1108-1110.

(Continued)

Primary Examiner — Sikarl A Witherspoon
(74) Attorney, Agent, or Firm — Joseph T. Leone, Esq.; DeWitt LLP

(57) ABSTRACT

A method of selectively reacting lignin or a lignin-derived reactant to yield an aromatic product. The method includes the step of reacting lignin or a lignin-derived reactant with a molybdenum-containing catalyst, in a solvent, and optionally in the presence of an oxidant, for a time and a temperature wherein at least a portion of the lignin or lignin-derived reactant is selectively converted into an aromatic product, preferably coniferaldehyde and/or sinapaldehyde.

42 Claims, 1 Drawing Sheet

(56) References Cited

OTHER PUBLICATIONS

Ragauskas et al., The path forward for biofuels and biomaterials. *Science* 2006, 311, 484-489.
Ragauskas et al., Lignin valorization: Improving lignin processing in the biorefinery. *Science* 2014, 344, 1246843.
Rahimi et al., Chemoselective metal-free aerobic alcohol oxidation in lignin. *Journal of the American Chemical Society* 2013, 135, 6415-6418.
Rahimi et al., Formic-acid-induced depolymerization of oxidized lignin to aromatics. *Nature* 2014, 515, 249-252.
Ralph et al., Determination of the conformation and isomeric composition of lignin model quinone methides by NMR. *Journal of Wood Chemistry and Technology* 1983, 3, 183-194.
Ralph et al., Simple preparation of 8-5-coupled diferulate. *Journal of Agricultural and Food Chemistry* 1998, 46, 2531-2532.
Rinaldi et al., Paving the way for lignin valorisation: Recent advances in bioengineering, biorefining and catalysis. *Angewandte Chemie (International Edition)* 2016, 55, 8164-8215.
Sanz et al., Simple and selective oxidation of thiols to disulfides with dimethylsulfoxide catalyzed by dichlorodioxomolybdenum(VI). *Synthesis-Stuttgart* 2002, 856-858.
Sanz et al., Selective deoxygenation of sulfoxides to sulfides with phosphites catalyzed by dichlorodioxomolybdenum(VI). *Synthesis-Stuttgart* 2004, 1629-1632.
Sedai et al., Comparison of copper and vanadium homogeneous catalysts for aerobic oxidation of lignin models. *ACS Catalysis* 2011, 1, 794-804.
Sedai et al., Aerobic oxidation of β-1 lignin model compounds with copper and oxovanadium catalysts. *ACS Catalysis* 2013, 3, 3111-3122.
Shuai et al., Formaldehyde stabilization facilitates lignin monomer production during biomass depolymerization. *Science* 2016, 354, 329-333.
Sutradhar et al., Iron(III) and cobalt(III) complexes with both tautomeric (keto and enol) forms of aroylhydrazone ligands: catalysts for the microwave assisted oxidation of alcohols. *RSC Advances* 2016, 6, 8079-8088.
Zakzeski et al., The catalytic valorization of lignin for the production of renewable chemicals. *Chemical Reviews* 2010, 110, 3552-3599.
Zakzeski et al., Catalytic lignin valorization process for the production of aromatic chemicals and hydrogen. *ChemSusChem* 2012, 5, 1602-1609.

\* cited by examiner

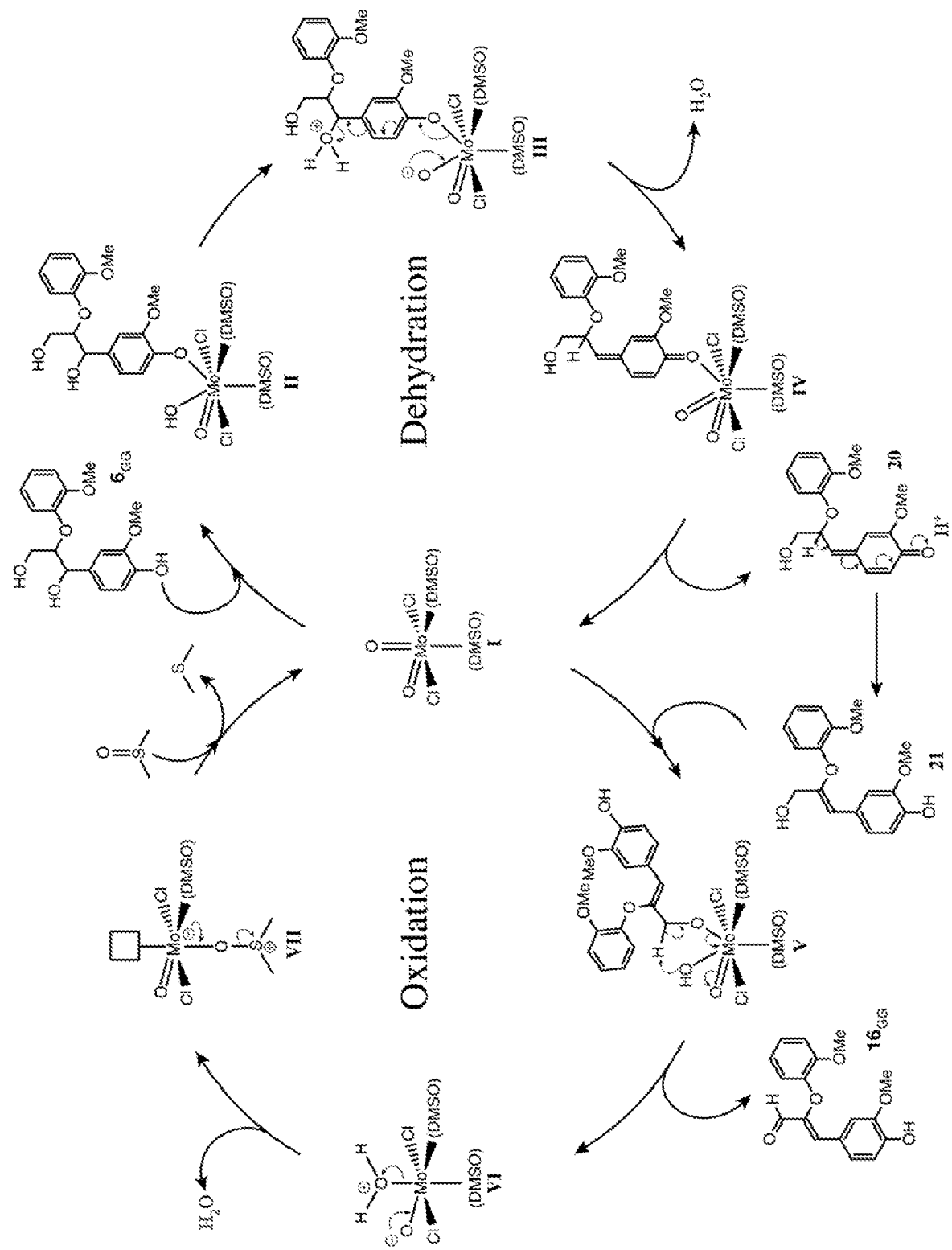

METHOD OF SELECTIVELY OXIDIZING LIGNIN

CROSS-REFERENCE TO RELATED APPLICATIONS

Priority is hereby claimed to provisional application Ser. No. 62/597,676, filed Dec. 12, 2017, which is incorporated herein by reference.

FEDERAL FUNDING STATEMENT

This invention was made with government support under DE-FC02-07ER64494 awarded by the US Department of Energy. The government has certain rights in the invention.

BACKGROUND

Lignin is the largest source of renewable aromatic compounds on the planet. In recent years, lignin has received increased attention in academia and industry for its potential to be converted into commodity chemicals. Whereas lignin has historically been burned to provide energy, new efforts have focused on utilizing and manipulating its inherent structure and functionality. See Boerjan, W.; Ralph, J.; Baucher, M., Lignin biosynthesis. *Annual Reviews in Plant Biology* 2003, 54, 519-546; Li, C. Z.; Zhao, X. C.; Wang, A. Q.; Huber, G. W.; Zhang, T., Catalytic transformation of lignin for the production of chemicals and fuels. *Chemical Reviews* 2015, 115, 11559-11624; Zakzeski, J.; Bruijnincx, P. C. A.; Jongerius, A. L.; Weckhuysen, B. M., The catalytic valorization of lignin for the production of renewable chemicals. *Chemical Reviews* 2010, 110, 3552-3599; Rinaldi, R.; Jastrzebshi, R.; Clough, M. T.; Ralph, J.; Kennema, M.; Bruijnincx, P. C. A.; Weckhuysen, B. M., Paving the way for lignin valorisation: Recent advances in bioengineering, biorefining and catalysis. *Angewandte Chemie (International Edition)* 2016, 55, 8164-8215; Ragauskas, A. J.; Beckham, G. T.; Biddy, M. J.; Chandra, R.; Chen, F.; Davis, M. F.; Davison, B. H.; Dixon, R. A.; Gilna, P.; Keller, M.; Langan, P.; Naskar, A. K.; Saddler, J. N.; Tschaplinski, T. J.; Tuskan, G. A.; Wyman, C. E., Lignin valorization: Improving lignin processing in the biorefinery. *Science* 2014, 344, 1246843; and Ragauskas, A. J.; Williams, C. K.; Davison, B. H.; Britovsek, G.; Cairney, J.; Eckert, C. A.; Frederick, W. J.; Hallett, J. P.; Leak, D. J.; Liotta, C. L.; Mielenz, J. R.; Murphy, R.; Templer, R.; Tschaplinski, T., The path forward for biofuels and biomaterials. *Science* 2006, 311, 484-489. For example, various strategies have shown promise in deriving valuable chemicals from the lignin portion of biomass feedstocks, including lignin catalytic cracking, hydrolysis, reduction/hydrogenolysis, and oxidation. See Zakzeski, J.; Jongerius, A. L.; Bruijnincx, P. C.; Weckhuysen, B. M., Catalytic lignin valorization process for the production of aromatic chemicals and hydrogen. *Chem Sus Chem* 2012, 5, 1602-1609; Shuai, L.; Amiri, M. T.; Questell-Santiago, Y. M.; Héroguel, F.; Li, Y.; Kim, H.; Meilan, R.; Chapple, C.; Ralph, J.; Luterbacher, J. S., Formaldehyde stabilization facilitates lignin monomer production during biomass depolymerization. *Science* 2016, 354, 329-333; and Badalyan, A.; Stahl, S. S., Cooperative electrocatalytic alcohol oxidation with electron-proton-transfer mediators. *Nature* 2016, 535, 406-410. Of these methods, oxidative treatments present several advantages and have the potential to yield more highly functionalized monomers or oligomers, which could be useful within the chemical industry. See, for example, Ma, R.; Xu, Y.; Zhang, X., Catalytic oxidation of biorefinery lignin to value-added chemicals to support sustainable biofuel production. *Chem Sus Chem* 2015, 8, 24-51; Lancefield, C. S.; Ojo, O. S.; Tran, F.; Westwood, N.J., Isolation of functionalized phenolic monomers through selective oxidation and C—O bond cleavage of the β-O-4 linkages in lignin. *Angewandte Chemie (International Edition)* 2015, 54, 258-262; Rahimi, A.; Azarpira, A.; Kim, H.; Ralph, J.; Stahl, S. S., Chemoselective metal-free aerobic alcohol oxidation in lignin. *Journal of the American Chemical Society* 2013, 135, 6415-6418; and Rahimi, A.; Ulbrich, A.; Coon, J. J.; Stahl, S. S., Formic-acid-induced depolymerization of oxidized lignin to aromatics. *Nature* 2014, 515, 249-252.

As this subfield of lignin valorization continues to mature, some promising homogeneous catalytic oxidation methods have emerged. Hanson et al. developed a series of oxovanadium catalysts featuring various ligands and successfully applied them to the oxidative cleavage of lignin. Depending on which catalyst they employed, the researchers were able to selectively cleave C—C or C—O bonds in phenolic lignin model compounds. Sedai, B.; Diaz-Urrutia, C.; Baker, R. T.; Wu, R. L.; Silks, L. A.; Hanson, S. K., Comparison of copper and vanadium homogeneous catalysts for aerobic oxidation of lignin models. *ACS Catalysis* 2011, 1, 794-804; Hanson, S. K.; Baker, R. T., Knocking on wood: base metal complexes as catalysts for selective oxidation of lignin models and extracts. *Accounts of Chemical Research* 2015, 48, 2037-2048; Hanson, S. K.; Wu, R. L.; Silks, L. A., C—C or C—O Bond cleavage in a phenolic lignin model compound: selectivity depends on vanadium catalyst. *Angewandte Chemie—International Edition* 2012, 51, 3410-3413; and Sedai, B.; Diaz-Urrutia, C.; Baker, R. T.; Wu, R. L.; Silks, L. A.; Hanson, S. K., Aerobic oxidation of β-1 lignin model compounds with copper and oxovanadium catalysts. *ACS Catalysis* 2013, 3, 3111-3122.

Mottweiler successfully used vanadium acetylacetonate and copper (II) nitrate as catalysts to cleave lignin model compounds and generate carboxylic acids in modest yields. Mottweiler, J.; Puche, M.; Rauber, C.; Schmidt, T.; Concepcion, P.; Corma, A.; Bolm, C., Copper- and vanadium-catalyzed oxidative cleavage of lignin using dioxygen. *Chemsuschem* 2015, 8, 2106-2113.

Bozell and coworkers improved the performance of cobalt-Schiff base complexes in the oxidation of lignin model compounds. Biannic, B.; Bozell, J. J., Efficient cobalt-catalyzed oxidative conversion of lignin models to benzoquinones. *Organic Letters* 2013, 15, 2730-2733. They demonstrated that Co(salen) complexes can selectively convert phenolic lignin models into benzoquinones in good yields. Due to low abundance of free phenolic moieties in lignin, however, this method generates these benzoquinones from isolated lignins in only very low yields.

Each of these catalytic oxidation methods, in which $O_2$ was used as the ultimate oxidant, offers unique opportunities for selective chemical synthesis depending on the transition metal and ligand scaffold. However, they are all limited by the long reaction times required even for the simplest of lignin model compounds. Efficient catalytic conversion of both lignin model compounds and lignin to well-defined aromatics represents a key challenge that has considerably limited the valorization of lignin. To date, this challenge remains long-felt and unmet.

Previously, dioxomolybdenum compounds have been reported as efficient catalysts for the oxidation of alcohols. See Jeyakumar, K.; Chand, D. K., Aerobic oxidation of benzyl alcohols by Mo—VI compounds. *Applied Organometallic Chemistry* 2006, 20, 840-844; Jeyakumar, K.;

Chand, D. K., Application of molybdenum(VI) dichloride dioxide (MoO$_2$Cl$_2$) in organic transformations. *Journal of Chemical Sciences* 2009, 121, 111-123; Enemark, J. H.; Cooney, J. J. A., Synthetic analogues and reaction systems relevant to the molybdenum and tungsten oxotransferases. *Chemical Reviews* 2004, 104, 1175-1200; Chen, C. T.; Kuo, J. H.; Ku, C. H.; Weng, S. S.; Liu, C. Y., Nucleophilic acyl substitutions of esters with protic nucleophiles mediated by amphoteric, oxotitanium, and vanadyl species. *Journal of Organic Chemistry* 2005, 70, 1328-1339; Sanz, R.; Escribano, J.; Aguado, R.; Pedrosa, M. R.; Anaiz, F. J., Selective deoxygenation of sulfoxides to sulfides with phosphites catalyzed by dichlorodioxomolybdenum(VI). *Synthesis—Stuttgart* 2004, 1629-1632; and Sanz, R.; Aguado, R.; Pedrosa, M. R.; Arnaiz, F. J., Simple and selective oxidation of thiols to disulfides with dimethylsulfoxide catalyzed by dichlorodioxomolybdenum(VI). *Synthesis—Stuttgart* 2002, 856-858. But, dioxomolybdenum compounds have not been used on lignin or even simple lignin model compounds. Recently, Sanz and coworkers reported on the oxidative cleavage of glycols catalyzed by a common and easily prepared dioxomolybdenum (VI) complex in dimethyl sulfoxide (DMSO) using microwave irradiation. See Garcia, N.; Rubio-Presa, R.; Garcia-Garcia, P.; Fernandez-Rodriguez, M. A.; Pedrosa, M. R.; Arnaiz, F. J.; Sanz, R., A selective, efficient and environmentally friendly method for the oxidative cleavage of glycols. *Green Chemistry* 2016, 18, 2335-2340. As an efficient and direct manner of heating the reaction mixture rapidly, microwave irradiation has already been successfully explored in organic synthesis and lignin pretreatments. See, for example, Conesa, T. D.; Campelo, J. M.; Clark, J. H.; Luque, R.; Macquarrie, D. J.; Romero, A. A., A microwave approach to the selective synthesis of omega-laurolactam. *Green Chemistry* 2007, 9, 1109-1113; Badamali, S. K.; Luque, R.; Clark, J. H.; Breeden, S. W., Microwave assisted oxidation of a lignin model phenolic monomer using Co(salen)/SBA-15. *Catalysis Communications* 2009, 10, 1010-1013; and Sutradhar, M.; Alegria, E. C. B. A.; Mahmudov, K. T.; Silva, M. F. t. C. G. d.; Pombeiro, A. J. L., Iron(III) and cobalt(III) complexes with both tautomeric (keto and enol) forms of aroylhydrazone ligands: catalysts for the microwave assisted oxidation of alcohols. *RSC Advances* 2016, 6, 8079-8088.

SUMMARY

Lignin, the most abundant renewable source of aromatic compounds on the planet, has been successfully transformed to generate valuable aromatic chemicals using various strategies. Homogeneous catalytic oxidation, in which the design of different transition metal-ligand complexes can yield variously substituted aromatics, offers new transformation opportunities that could find application within the chemical industry. Many such catalysts, however, fail to convert lignin to well-defined aromatics efficiently. Recognizing the need for more efficient and selective chemical transformation of lignin, disclosed herein is a microwave-assisted, catalytic oxidation system using easily prepared molybdenum catalyst such as MoO$_2$Cl$_2$(DMSO)$_2$ as the catalyst. The reaction can be run in a number of different solvents, either with or without additional oxidants. For example, DMSO functions as both the solvent and oxidant in the subject method. The method has been shown to transform very efficiently a series of lignin model compounds containing the units and functional groups found in native and processed lignins. The electron density of the oxidation substrates influenced the selectivity of β-ether phenolic dimer cleavage to generate sinapaldehyde and coniferaldehyde, monomers not usually produced by oxidative methods. Time-course studies on two key intermediates revealed important insight into the reaction pathway. Due to the broad scope of this oxidation system and the insight gleaned with regard to its mechanism, this strategy is applicable generically to producing useful aromatic chemicals from lignin. In short, disclosed herein is a selective and efficient catalytic approach to the oxidation of lignin and lignin model compounds using microwave irradiation technology and molybdenum-containing catalysts.

Thus, disclosed herein is a method of selectively reacting lignin or a lignin-derived reactant to yield an aromatic product. The method comprises reacting lignin or a lignin-derived reactant with a molybdenum-containing catalyst, in a solvent, and optionally in the presence of an oxidant, for a time and a temperature wherein at least a portion of the lignin or lignin-derived reactant is selectively converted into an aromatic product. The molybdenum-containing catalyst may be selected from MoO$_2$Cl$_2$(DMSO)$_2$, MoO$_3$, Na$_2$MoO$_4$.2H$_2$O, MoO$_2$Cl$_2$, [C$_5$H$_5$Mo(CO)$_3$]$_2$, and/or Mo(dppf)(CO)$_4$.

The reaction can be conducted at a range of temperatures, generally from about 120° C. to about 250° C., more preferably from about 120° C. to about 200° C., and more preferably still from about 120° C. to about 160° C. Running the reaction above and below these preferred temperature ranges is within the scope of the method disclosed and claimed herein. It is preferred that the reaction temperature is established by microwave irradiation, although radiant heating will yield the same results (but with longer reaction times).

The reaction is conducted in a non-aqueous solvent, preferably a non-protic polar solvent such as dimethyl sulfoxide (DMSO), gamma-valerolactone (GVL), dimethylformamide (DMF), or cyclohexanone. DMSO is the preferred solvent because it can function as both the solvent and as an oxidizing agent to drive the reaction. If DMSO is used as the solvent, the lignin or lignin-derived reactant may be reacted with the molybdenum-containing catalyst in the absence of any additional oxidizing agents. When the solvent is something other than DMSO, it is generally preferred that the lignin or lignin-derived reactant is reacted with the molybdenum-containing catalyst in the presence of an added oxidizing agent. The oxidizing agent is preferably DMSO, O$_2$, hydrogen peroxide, benzoyl peroxide, or ammonium persulfate.

The preferred product mixture comprises, among other aromatic products, coniferaldehyde and sinapaldehyde.

BRIEF DESCRIPTION OF THE DRAWING

The sole drawing FIGURE is a proposed mechanism for the reactions described herein. Note, however, that the method is not limited to any underlying mechanism or physical phenomenon.

DETAILED DESCRIPTION

Definitions and Abbreviations

COSY=gradient-selected correlation spectroscopy. DDQ=2,3-dichloro-5,6-dicyanobenzoquinone. DMF=dimethylformamide. DMSO=dimethylsulfoxide. DPPF=bis(diphenylphosphino) ferrocene. EtOAc=ethyl acetate. GVL=gamma-valerolactone. HMBC=heteronuclear multiple-bond correlation. HSQC=heteronuclear single-quantum coherence. NMR=nuclear magnetic resonance.

Lignin and Lignin-Derived: "Lignin" refers to the natural, cross-linked complex organic polymers that form the principal structural framework in the support tissues of vascular plants. The composition of lignin differs from species to species. Generally speaking, it is a natural, heterogeneous polymer comprised mainly of three monomers: paracoumaryl alcohol (4-(3-hydroxy-1-propenyl)phenol), coniferyl alcohol (4-(3-hydroxy-1-propenyl)-2-methoxyphenol), and sinapyl alcohol (4-(3-hydroxyprop-1-enyl)-2,6-dimethoxyphenol). "Lignin-derived" refers to any compound or composition made from lignin via chemical, thermal, and/or mechanical means.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 1 to 9, from 3.6 to 4.6, from 3.5 to 9.9, and so forth.

All references to singular characteristics or limitations of the present invention shall include the corresponding plural characteristic or limitation, and vice-versa, unless otherwise specified or clearly implied to the contrary by the context in which the reference is made. The indefinite articles "a" and "an" mean "one or more."

All combinations of method or process steps as used herein can be performed in any order, unless otherwise specified or clearly implied to the contrary by the context in which the referenced combination is made.

The methods disclosed herein can comprise, consist of, or consist essentially of the essential elements and limitations of the method described herein, as well as any additional or optional ingredients, components, or limitations described herein or otherwise useful in organic chemistry. For example, the reaction may optionally be conducted in the presence (and thus also in the absence) of an oxidant. Thus, the method may consist of or consist essentially of the remaining steps, in the absence of an oxidant in the reaction mix.

The Method:

Initial reactivity studies were conducted on an all-syringyl (S—S) β-O-4-linked phenolic dimer $6_{SS}$ (see Table 1) using the easily prepared dioxomolybdenum (VI) complex, $MoO_2Cl_2(DMSO)_2$ in DMSO as solvent, along with an oxidant. It was found that the oxidation of these dimers in DMSO at 160° C. for 4 h (catalyzed by adding 5 mol % $MoO_2Cl_2(DMSO)_2$) generated sinapaldehyde $12_S$ (3,5-dimethoxy-4-hydroxy-cinnamaldehyde) in an isolated yield of 85%. When traditional radiant heating was replaced with microwave irradiation in this catalytic system, similar results were obtained after only 10 minutes at the same temperature. These findings are all the more remarkable in light of the fact that no other reported method can oxidize β-O-4 phenolic dimers in such an efficient and selective manner. Moreover, this method is the first to generate sinapaldehyde $12_S$ directly from the oxidation of these model dimers. The method thus has commercial value to produce value-added aromatic compounds from lignin.

TABLE 1

Model Lignin Compounds and Reaction Products

| SUBSTRATE | Rxn Time (Min) | PRODUCTS |
|---|---|---|
| 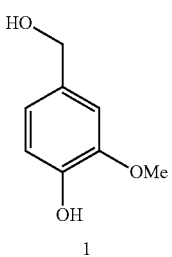 [SMILES: COc1cc(CO)ccc1O]<br>1 | 10 | 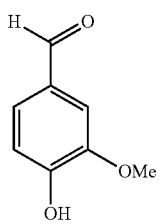<br>11 92% |
| 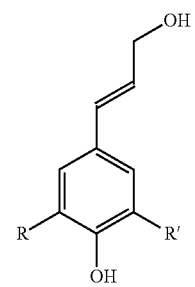<br>$2_H$ R = R' = H<br>$2_G$ R = H, R' = OMe<br>$2_S$ R = R' = OMe | 10 | 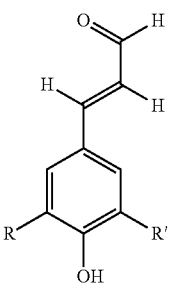<br>$12_H$ 97%<br>$12_G$ 91%<br>$12_S$ 87% |

TABLE 1-continued

Model Lignin Compounds and Reaction Products

| SUBSTRATE | Rxn Time (Min) | PRODUCTS |
|---|---|---|
| 3 | 10 | 13 90% |
| 4 | 10 | 14 65% (cis:trans = 97:3) |
| $5_G$ R = H<br>$5_{G'}$ R = Me | 20 | $15_G$ 86%<br>$15_{G'}$ 85% |
| $6_{GG}$ R = R' = H<br>$6_{GS}$ R = H, R' = H<br>$6_{SG}$ R = OMe, R' = H<br>$6_{SS}$ R = R' = OMe | 10 | $16_{GG}$ 81%    $12_G$ 0      $18_G$ 0<br>$16_{GS}$ 0       $12_G$ 83%   $18_S$ 76%<br>$16_{SG}$ 32%    $12_S$ 53%   $18_G$ 49%<br>$16_{SS}$ 0       $12_S$ 87%   $18_S$ 81% |

TABLE 1-continued

Model Lignin Compounds and Reaction Products

| SUBSTRATE | Rxn Time (Min) | PRODUCTS |
|---|---|---|
| $7_{G'}$ R = H<br>$7_{S'}$ R = OMe | 10 | $17_{G'}$ 93% (=$5_{G'}$)<br>$17_{S'}$ 93% |
| 8 | 10 | $12_S$ 91%° |
| 9 | 15 | 19 87% |

TABLE 1-continued

Model Lignin Compounds and Reaction Products

| SUBSTRATE | Rxn Time (Min) | PRODUCTS |
|---|---|---|
| 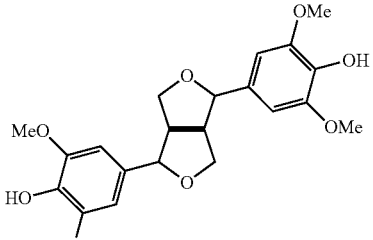<br>10 | 15 | NR |

In Table 1, substrates are numbered 1-10 and their corresponding products are numbered from 11-20.
[a] Reactions were conducted with 0.5 mmol model compounds, 5 mol % MoO$_2$Cl$_2$(DMSO)$_2$ in 5 mL DMSO under microwave irradiation (400 W), isolated yields.
[b] Two equivalents of sinapaldehyde were formed.

Encouraged by these initial results, the microwave reaction conditions were optimized using this same phenolic S—S β-ether dimer $6_{SS}$. See the Examples section, Table 2 below, for complete details on the catalyst, solvent, oxidants, and temperature screening data and full reaction conditions. After screening at various microwave temperatures, it was found that the reaction generated sinapaldehyde $12_S$ most efficiently between 120° C. and 160° C. The α-ketone (not shown, but S—S analog of 5 or 17) was generated as a byproduct at the lower end of that temperature range.

DMSO is the most suitable solvent, although others, including gamma-valerolactone (GVL), dimethylformamide (DMF), and cyclohexanone (each optionally and preferably containing and additional oxidant, such as 3.0 equivalents of DMSO) may also be used. DMSO is preferred because it gives the highest yields and simultaneously acts as both the solvent and the oxidant. Other oxidants, such as O$_2$, hydrogen peroxide, benzoyl peroxide, and ammonium persulfate may also be used, but do not afford sinapaldehyde $12_S$ in yields as high as did DMSO.

Under the optimized reaction conditions (Table 2, entry 5), other commercially available molybdenum complexes (such as MoO$_3$, Na$_2$MoO$_4$.2H$_2$O, and MoO$_2$Cl$_2$) showed high oxidative reactivity but lower selectively, affording sinapaldehyde $12_S$ in yields of 50-75%, with the corresponding α-ketone (not shown, but S—S analog of 5 or 17) and unknown polymeric byproducts comprising the remainder.

With these optimized conditions in hand, the reaction was further explored using a range of lignin model compounds containing the key units and functional groups commonly found in native and processed lignins. See Table 1. The catalytic system performed very well using a series of simple model compounds as the reactant: oxidation of the primary benzylic alcohol 1 (entry 1) and the three "traditional" lignin monomers (p-coumaryl alcohol $2_H$, coniferyl alcohol $2_G$, and sinapyl alcohol $2_S$) afforded the corresponding aldehydes, p-coumaraldehyde $12_H$ (4-hydroxycinnamaldehyde), coniferaldehyde $12_G$ (4-hydroxy-3-methoxycinnamaldehyde) and sinapaldehyde $12_S$, in isolated yields of 87-97%. No acid by-products (produced by over-oxidation) were detected. This oxidation, with its high yields of hydroxycinnamaldehydes 12 from the hydroxycinnamyl alcohols (monolignols, 2), is synthetically useful; it competes with the likes of 2,3-dichloro-5,6-dicyanobenzoquinone-mediated oxidation (DDQ-mediated oxidation) to elicit such oxidations. (See Kumar, N. S. S.; Varghese, S.; Narayan, G.; Das, S., Hierarchical self-assembly of donor-acceptor-substituted butadiene amphiphiles into photoresponsive vesicles and gels. *Angewandte Chemie—International Edition* 2006, 45, 6317-6321.)

Interestingly, in contrast to the current observance of the α-ketone 17 in product mixtures from the oxidation of non-phenolic dimers 7, the present work produced evidence of dehydration of the benzylic alcohols 3 or 4 to form styrene 13 or styryl ether 14 products in good yields. More significantly, these oxidation conditions proved to be highly effective on β-ether dimers containing diols, i.e., with the full 3-carbon sidechain that is the common chemical motif in lignin. Both the syringyl- and guaiacyl-type phenolic dimers 6 demonstrated good reactivity but with strikingly different product profiles. Oxidation of phenolic G-G β-ether dimer $6_{GG}$ afforded the cinnamaldehyde-β-aryl ether $16_{GG}$ (a valuable product allowing simpler C$_\beta$—O bond cleavage) in a yield of 81% without any cleavage products detectable by NMR. Conversely, the oxidation of phenolic G-S- and S—S-β-O-4 dimers $6_{GS}$ and $6_{SS}$ yielded solely the cinnamaldehydes $12_G$ and $12_S$, corresponding to C$_\beta$—O bond cleavage, and syringol $18_S$ (2,6-dimethoxyphenol) in high yields. In contrast, oxidation of the S-G-model $6_{SG}$ afforded both the cinnamaldehyde-β-aryl ether $16_{SG}$ (32%) and partial C$_\beta$—O bond cleavage to produce sinapaldehyde $12_S$ and guaiacol $18_G$.

These results provided important insight into the dependence of the product distribution on the electron density of the reactant: substrates with more electron-rich B-rings produced a less-stable cinnamaldehyde-β-aryl ether, which cleaved to form the respective cinnamaldehyde and phenol. As evidence of this dependence, two equivalents of sinapaldehyde $12_S$ were obtained in an isolated yield of 91% following the oxidation of the authentic sinapyl alcohol β-O-4 dimer 8 under the optimized conditions. In the case of both G-type and S-type non-phenolic β-ether dimers $7_{G'}$ and $7_{S'}$, the α-ketone was detected in high yield (93%) after 10 minutes, although dehydration of the γ-alcohol began to occur after a reaction time of 25 minutes.

As expected based on these results, oxidation of α-keto-γ-hydroxy model compounds $5_G$ and $5_{G'}$ offered further proof that benzylic oxidation takes place first, followed by dehydration to afford the alkene. The oxidation of another important lignin model 9 featuring the β-5 linkage showed highly selective oxidation of the cinnamyl alcohol sidechain to yield the corresponding cinnamaldehyde. However, this reaction system did not cleave a sinapyl alcohol β-β-coupled dimer 10 (syringaresinol), regardless of reaction time; in this case, only the starting material was detected.

The mechanistic details of the catalytic cycle were then probed using the phenolic G-G β-ether dimer model compound $6_{GG}$. See the sole drawing FIGURE for the complete proposed mechanism. Note that the proposed mechanism is for sake of discussion only. The method claimed herein is not limited to any specific underlying mechanism or transition state. Quinone methide 20 and cinnamyl alcohol-β-aryl ether 21 were synthesized and fully characterized as important intermediates, and $^1$H NMR spectroscopy was used to obtain reaction time-course data. Direct investigation of the oxidation of β-ether dimer $6_{GG}$ revealed a low steady-state concentration of the cinnamyl alcohol-β-ether 21 throughout the formation of the cinnamaldehyde-β-aryl ether $16_{GG}$. See the drawing. The data also indicated that the oxidation process begins with the conversion of the starting dimer $6_{GG}$ to its quinone methide 20, which quickly undergoes conversion to cinnamyl alcohol-β-aryl ether 21, followed by oxidation to afford the final product $16_{GG}$ (see the drawing). The overall reaction from reactant $6_{GG}$ to product $16_{GG}$ is:

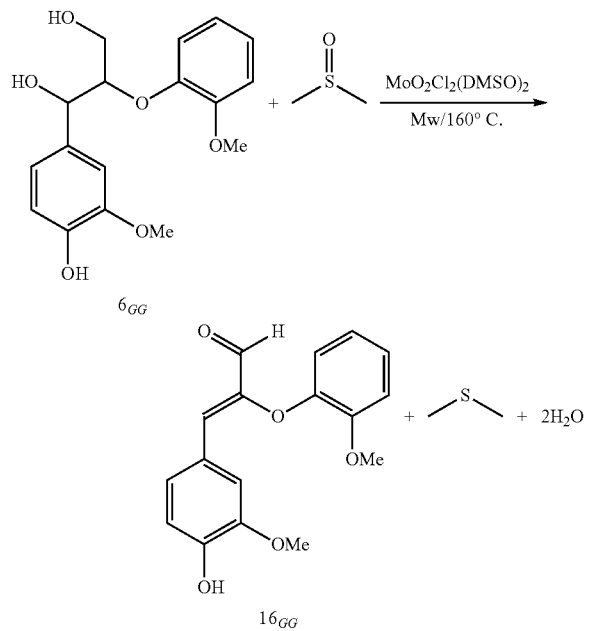

Independent studies following the oxidation of both authentic synthesized quinone methide 20 to final product $16_{GG}$, and the cinnamyl alcohol-β-aryl ether 21 to final product $16_{GG}$, also confirmed these findings. Kinetic studies provided evidence of the rapid conversion of 20 to 21, and demonstrated that intermediate 21 is consumed more rapidly than the overall conversion of the starting dimer into the product. These findings suggest that the formation of quinone methide 20 is the rate-limiting step in this reaction.

A plausible mechanism for the formation of cinnamaldehyde-β-aryl ether $16_{GG}$ is given in the drawing. The catalytic cycle first undergoes the dehydration, which begins with the coordination of the phenol unit of the β-ether dimer $6_{GG}$ to the molybdenum center to form compound II, and is then followed by proton transfer to generate intermediate III. Next, a quinone methide-catalyst complex IV forms by water elimination involving the cleavage of the C—O bond. The intermediate quinone methide 20 rapidly undergoes Hp elimination to form intermediate 21, which will coordinate to the Mo center and undergo the oxidation process to produce the product $16_{GG}$ and metal complex VI. The intermediate VI eliminates one molecule of water to generate complex VII. DMSO then occupies the empty site to regenerate the catalyst I, with the release of dimethyl sulfide as a byproduct.

In summary, the overall process of the oxidation of a phenolic β-ether dimer involves the oxidation of two alcohols (by DMSO if using it as a solvent and/or oxidant), generating two molecules of water and one molecule of dimethyl sulfide as the only byproducts. Oxidation of non-phenolic β-ether dimers 7 cannot follow this mechanism; the reaction stops after benzylic oxidation to produce the α-ketone (e.g., compounds 7 to 17).

Thus, disclosed herein is an effective and efficient method for the oxidation of lignin and lignin model compounds using easily prepared and environmentally friendly molybdenum complexes, such as $MoO_2Cl_2(DMSO)_2$ as a catalyst and DMSO as the preferred solvent and oxidant. (As noted above, other solvent/oxidant combinations may also be used.) This method can oxidize lignin as well as a broad range of lignin model compounds. Its ability to cleave the C—O bond in phenolic β-ether dimers to form sinapaldehyde or coniferaldehyde has industrial utility for converting lignin, and lignin-derived intermediates into value-added aromatic compounds. Reaction time-course studies of two key synthetic intermediates provided important insights into the mechanism. Extrapolating from its broad reaction scope and the mechanistic details, this new catalytic system facilitates depolymerization of lignin into commodity chemicals.

EXAMPLES

The following Examples are included to provide a more complete description of the method described and claimed herein. The Examples, however, are not intended to limit the scope of the claims in any fashion.

General Considerations:

All reactions were assembled under air atmosphere unless otherwise noted. All organic substrates and solvents were purchased from commercial sources and used without further purification. Flash chromatography was performed with Biotage®-brand snap silica cartridges on an Isolera One-brand flash chromatogram (Biotage, Charlottesville, Va., USA). NMR spectra were acquired on a Bruker Biospin (Billerica, Mass., USA) AVANCE-III 500 MHz and 700 MHz spectrometers equipped with a 5 mm cryogenic TCI (500) or a QCI $^1H/^{31}P/^{13}C/^{15}N$ (700) gradient probe with inverse geometry (proton coil closest to the sample). Proton and carbon NMR spectral processing was performed using MestReNova-brand software (Mestrelab Research, S.L., Santiago de Compostela, Spain) and 2D spectral processing was performed using Bruker's Topspin 3.5-brand software. The central solvent peaks were used as internal reference ($\delta_H/\delta_C$: acetone-$d_6$, 2.04/29.84; $D_2O$, 4.79, and DMSO-$d_6$, 2.50/39.51). The standard Bruker implementations of 1D and 2D (gradient-selected correlation spectroscopy (COSY), heteronuclear single-quantum coherence (HSQC), and heteronuclear multiple-bond correlation (HMBC)) NMR experiments were used for routine structural assignments of newly synthesized compounds. The microwave heating was performed in a microwave reactor (MARS 5-brand, CEM Corporation, Matthews, N.C., USA) with a single-model microwave cavity producing continuous irradiation (temperature measurements were conducted using an IR sensor located below the microwave cavity floor), and reaction times refer to the total hold time at the indicated temperature.

Preparation of Catalyst MoO$_2$Cl$_2$(DMSO)$_2$:

The catalyst was prepared by the typical procedure as follows: 100 mL of distilled water and 100 mL of concentrated (12 M) hydrochloric acid was added to 20.0 g (0.138 mol) of MoO$_3$ powder. This mixture was heated to just below boiling with mechanical stirring until the MoO$_3$ has dissolved (2 h) and the resulting solution was cooled to room temperature. 50.0 mL (0.705 mol) of dimethyl sulfoxide was added with mechanical stirring. After 15 min the white, microcrystalline precipitate was collected by suction filtration, washed with acetone (4×30 mL), and dried in vacuum. Yield: 43 g (86%). (See Garcia, N.; Rubio-Presa, R.; Garcia-Garcia, P.; Fernandez-Rodriguez, M. A.; Pedrosa, M. R.; Arnaiz, F. J.; Sanz, R., A selective, efficient and environmentally friendly method for the oxidative cleavage of glycols. *Green Chemistry* 2016, 18, 2335-2340.)

Preparation of Quinone Methide 20:

Compound 20 (Quinone Methide):

Quinone methide 20 was prepared by a method analogous to that of Ralph and Adams. (See Ralph, J.; Adams, B. R., Determination of the conformation and isomeric composition of lignin model quinone methides by NMR. *Journal of Wood Chemistry and Technology* 1983, 3, 183-194.) Chloroform (20 mL) containing compound 6$_{GG}$ (0.3 mmol, 96 mg) was placed in the 125 mL separatory funnel, and then bromotrimethylsilane (0.5 mmol, 76 mg) was added with swirling. The resulting solution was kept for 1 h and then cold saturated aqueous NaHCO$_3$ solution was added and thoroughly mixed. The chloroform layer was separated, dried over MgSO$_4$, and evaporated under vacuum. Pure compound 20 (~100% yield) was collected as the yellow solid without further purification (syn: anti=7:3). syn-Isomer: NMR (500 MHz, acetone-d$_6$) $\delta_H$: 3.71 (3H, s, OCH$_3$), 3.82 (3H, s, OCH$_3$'), 3.8-4.02 (2H, m, γ), 4.22 (1H, m, β), 6.27 (1H, d, J=9.67 Hz, H5), 6.45 (1H, d, J=8.46 Hz, Hα), 6.52 (1H, d, J=2.2 Hz, H2), 6.79-6.99 (4H, m, H1', H2', H5' and H6'), 7.20 (1H, dd, J=2.2 and 9.67 Hz, H6); $\delta_C$: 55.42 (OCH$_3$), 56.12 (OCH$_3$'), 64.96 (Cγ), 78.52 (Cβ), 105.93 (C2), 113.42 (C2'), 118.72 (C5), 121.75 (C6'), 123.53 (C1'), 128.57 (Cα), 134.74 (C1), 142.12 (C5), 144.05 (C6), 147.91 (C4'), 151.72 (C3'), 153.97 (C3), 180.84 (C4). HR-MS (ESI) calcd for C$_{17}$H$_{18}$O$_5$ [(M+H)$^+$]: 303.1227; found: 303.1221. anti-Isomer: NMR (500 MHz, acetone-d$_6$) $\delta_H$: 3.69 (3H, s, OCH$_3$), 3.82 (3H, s, OCH$_3$'), 3.8-4.02 (2H, m, Hγ), 4.22 (1H, m, Hβ), 6.30 (1H, d, J=9.67 Hz, H5), 6.30 (1H, d, J=8.46 Hz, Hα), 6.50 (1H, d, J=2.2 Hz, H2), 6.79-6.99 (4H, m, H1', H2', H5' and H6'), 7.69 (1H, dd, J=2.2 and 9.67 Hz, H6); $\delta_C$: 55.42 (OCH$_3$), 56.12 (OCH$_3$'), 64.96 (Cγ), 78.52 (Cβ), 112.81 (C2), 113.46 (C2'), 119.22 (C5), 121.75 (C6'), 123.71 (C1'), 129.72 (Cα), 134.74 (C1), 142.12 (C5), 143.80 (C6), 147.82 (C4'), 151.88 (C3'), 153.27 (C3), 181.06 (C4). HR-MS (ESI) calcd for C$_{17}$H$_{18}$O$_5$ [(M+H)$^+$]: 303.1227; found: 303.1221.

Preparation of Intermediate 21

A mixture of DMSO (5 mL), the model compound 6$_{GG}$ (96 mg 0.3 mmol), K$_2$CO$_3$ (62 mg, 0.45 mmol) and MoO$_2$Cl$_2$(DMSO)$_2$ (4 mg, 5 mol %) was irradiated in 50 mL HP-500 vessel in the microwave cavity at the reported temperature for 5 min. The reaction mixture was cooled to room temperature and 20 mL water was added. The mixture was extracted in ethyl acetate (3×15 mL). The combined organic layers were washed with water and then satd. brine to completely remove the excess of DMSO, dried over anhydrous Na$_2$SO$_4$, filtered, and then the solvents were removed under reduced pressure. The crude products were purified through a 50 g silica-gel column by flash chromatography (n-hexanes/EtOAc=2:1) to obtain compound 21 as a yellow oil in 65% yield. NMR (500 MHz, acetone-d$_6$): $\delta_H$ 3.66 (3H, s, OCH$_3$), 3.86 (3H, s, OCH'$_3$), 4.11 (2H, d, J=6.25 Hz, Hγ), 6.20 (1H, S, Hα), 6.70 (1H, d, J=8.28 Hz, H5), 6.80 (1H, m, H6'), 6.93-6.98 (3H, m, H6, H1' and H5'), 7.03 (1H, d, J=8.07 Hz, H2'), 7.29 (1H, d, J=2.2 Hz, H2), 7.60 (1H, S, OH); $\delta_C$: 55.77 (OCH$_3$), 56.18 (OCH$_3$'), 61.90 (γ), 112.48 (C2), 113.54 (C2'), 114.13 (Cα), 115.48 (C5), 116.63 (C5'), 121.56 (C6'), 122.96 (C6), 123.56 (C1'), 127.66 (C1), 145.90 (C4'), 146.58 (C4), 147.90 (C3), 150.08 (C3'), 151.08 (Cβ). HR-MS (ESI) calcd for C$_{17}$H$_{18}$O$_5$ [(M+Na)$^+$]: 325.1046; found: 325.1043.

Catalyst Screening and Optimizing the Oxidation of β-Ether Model Compound 6$_{SS}$:

The oxidation of lignin model compound 6$_{SS}$ was carried out in the presence of related Mo compounds. Additional variables considered included temperature (from room temperature to 160° C.), solvent (DMSO, DMF and gamma-valerolactone (GVL)), oxidants (O$_2$, hydrogen peroxide, benzoyl peroxide) and additive (K$_2$CO$_3$, formic acid). A summary of the results is provided in Table 2.

TABLE 2

Mo-catalyzed oxidative cleavage of lignin model compound 6$_{SS}$

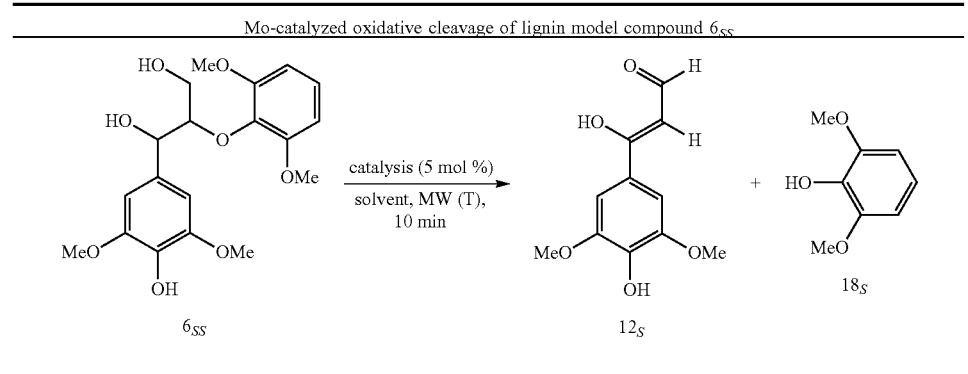

| | | | | | Yield$^a$ (%) | |
|---|---|---|---|---|---|---|
| Entry | Catalyst | Solvent | Oxidant/additive | Temp. (°C) | 12$_S$ | 18$_S$ |
| 1 | MoO$_2$Cl$_2$(DMSO)$_2$ | DMSO | — | 120 | 15 | 16 |
| 2 | MoO$_2$Cl$_2$(DMSO)$_2$ | DMSO | — | 130 | 55 | 57 |
| 3 | MoO$_2$Cl$_2$(DMSO)$_2$ | DMSO | — | 140 | 72 | 61 |
| 4 | MoO$_2$Cl$_2$(DMSO)$_2$ | DMSO | — | 150 | 89 | 85 |

TABLE 2-continued

Mo-catalyzed oxidative cleavage of lignin model compound $6_{SS}$

[Reaction scheme: compound $6_{SS}$ → catalysis (5 mol %), solvent, MW (T), 10 min → $12_S$ + $18_S$]

| Entry | Catalyst | Solvent | Oxidant/additive | Temp. (°C) | Yield$^a$ (%) $12_S$ | $18_S$ |
|---|---|---|---|---|---|---|
| 5 | MoO$_2$Cl$_2$(DMSO)$_2$ | DMSO | — | 160 | 95 | 93 |
| 6 | — | DMSO | — | 160 | 0 | 0 |
| 7 | MoO$_2$Cl$_2$(DMSO)$_2$ | GVL | DMSO (3 eq.) | 160 | 53 | 41 |
| 8 | MoO$_2$Cl$_2$(DMSO)$_2$ | DMF | DMSO (3 eq.) | 160 | 57 | 35 |
| 9$^b$ | MoO$_2$Cl$_2$(DMSO)$_2$ | DMF | O$_2$ | 160 | 43 | 36 |
| 10 | MoO$_2$Cl$_2$(DMSO)$_2$ | DMF | H$_2$O$_2$ | 160 | 15 | 0 |
| 11 | MoO$_2$Cl$_2$(DMSO)$_2$ | DMF | benzoyl peroxide | 160 | 23 | 0 |
| 12 | MoO$_2$Cl$_2$(DMSO)$_2$ | DMSO | K$_2$CO$_3$ (4 eq.) | 160 | 0 | 0 |
| 13 | MoO$_2$Cl$_2$(DMSO)$_2$ | DMSO | formic acid (4 eq.) | 160 | 0 | 0 |
| 14 | MoO$_3$ | DMSO | — | 160 | 66 | 53 |
| 15 | Na$_2$MoO$_4$*2H$_2$O | DMSO | — | 160 | 74 | 62 |
| 16 | MoO$_2$Cl$_2$ | DMSO | — | 160 | 58 | 54 |
| 17 | [C$_5$H$_5$Mo(CO)$_3$]$_2$ | DMSO | — | 160 | 53 | 37 |
| 18 | Mo(dppf)(CO)$_4$ | DMSO | — | 160 | 35 | 12 |

$^a$Yields were determined by $^1$H NMR spectroscopy (500 MHz) from the crude reaction mixture, internal standard = hexamethylbenzene. Reactions were conducted with 0.5 mmol of model compound $6_{SS}$ under microwave irradiation (400 W). No reaction occurred below 120° C.
$^b$ The reaction was performed in Schlenk tube charged with O$_2$ (1 atm) and heated in a sand-bath overnight.

General Procedure for Catalytic Oxidation of Lignin Model Compounds:

A mixture of DMSO (5 mL), the corresponding lignin model compound (1 mmol), and MoO$_2$Cl$_2$(DMSO)$_2$ (5 mol %) was irradiated in a 50 mL HP-500 vessel in the microwave cavity at the reported temperature for the required time (Table 2). The reaction mixture was cooled to room temperature and 20 mL water was added. The mixture was extracted by ethyl acetate (3×15 mL). The combined organic layers were washed with water and then saturated brine to completely remove the excess of DMSO, dried over anhydrous Na$_2$SO$_4$, filtered, and then the solvents were removed under reduced pressure. The crude products were purified through a 50 g silica-gel column by flash chromatography (n-hexanes/EtOAc). For the reactions carried out in DMSO-d$_6$ the crude mixture was analyzed by NMR after cooling to room temperature.

Analysis of the Reaction Time-Course with Compounds $6_{GG}$, 20, and 21:

Time-Course Study for the Reaction of $6_{GG}$.

A 15 mL thick-walled glass tube with a stir bar was charged with compound $6_{GG}$ (0.3 mmol, 96 mg), 5 mol % MoO$_2$Cl$_2$(DMSO)$_2$ (4 mg), and 10 mL DMSO-d$_6$. The tube was sealed with a rubber septum. The reaction mixture was heated at 160° C. Aliquots (0.4 mL) of the reaction mixture were taken through the septum with a long needle at set time intervals and transferred to the NMR tube containing triethylsilane (0.01 mmol, 1.16 mg) as internal standard.

Time Course Study for the Oxidation Reaction of 20.

A 15 mL thick-walled glass tube with a stir bar was charged with compound 20 (0.3 mmol, 91 mg), 5 mol % MoO$_2$Cl$_2$(DMSO)$_2$ (4 mg), and 10 mL DMSO-d$_6$. The tube was sealed with a rubber septum. The reaction mixture was heated at 160° C. and 0.4 mL of reaction mixture was taken through the septum with a long needle at set time intervals and were placed to the NMR tube containing triethylsilane (0.01 mmol, 1.16 mg) as internal standard.

Time Course Study for the Oxidation Reaction of 21.

A 15 mL thick-walled glass tube with a stir bar was charged with compound 21 (0.3 mmol, 91 mg), 5 mol % MoO$_2$Cl$_2$(DMSO)$_2$ (4 mg), and 10 mL DMSO-d$_6$. The tube was sealed with a rubber septum. The reaction mixture was heated at 160° C. and 0.4 mL of reaction mixture was taken through the septum with a long needle at set time intervals and were placed to the NMR tube containing triethylsilane (0.01 mmol, 1.16 mg) as internal standard.

Model Compounds:

The model compounds in Table 1 were all synthesized by standard methods. The β-ether dimeric models 5-8, were prepared as described previously. (Nakatsubo, F.; Sato, K.; Higuchi, T., Synthesis of guaiacylglycerol-β-guaiacyl ether. *Holzforschung* 1975, 29, 165-8.) Dehydrodiconiferyl alcohol (9, β-5 model) was synthesized via 8-5-coupled dehydrodiferulate (Ralph, J.; Garcia-Conesa, M. T.; Williamson, G., Simple preparation of 8-5-coupled diferulate. *Journal of Agricultural and Food Chemistry* 1998, 46, 2531-2532), followed by reduction of the esters with DiBAL-H. (Quideau, S.; Ralph, J., Facile large-scale synthesis of coniferyl, sinapyl, and p-coumaryl alcohol. *Journal of Agricultural and Food Chemistry* 1992, 40, 1108-1110.) Syringaresinol (10, β-β model) was produced via the radical coupling of sinapyl alcohol. (Freudenberg, K.; Neish, A. C. *Constitution and Biosynthesis of Lignin*; Springer-Verlag: Berlin-Heidelberg-New York, 1968.)

NMR Characterization of Selected Compounds:

Compound 11.

NMR (500 MHz, acetone-$d_6$): $\delta_H$ 3.89 (3H, s, 3OMe), 7.00 (1H, d, J=8.2 Hz, 5), 7.42 (1H, d, J=2.3 Hz, 2), 7.44 (1H, dd, J=8.0, 2.0 Hz, 6), 8.71 (1H, s, 4OH), 9.80 (1H, s, 11); $\delta_C$ 56.2 (3OMe), 110.7 (6), 115.9 (5), 127.0 (2), 130.5 (1), 148.8 (3), 153.4 (4), 191.2 (7). HR-MS (ESI) calcd for $C_8H_8O_3$ [(M−H)$^-$]: 150.9006; found: 150.9005.

Compound $12_H$.

NMR (500 MHz, acetone-$d_6$): $\delta_H$ 6.78 (1H, dd, J=16.0, 7.6 Hz, β), 7.42-7.51 (3H, m, 3, 5, 4OH), 7.67 (1H, d, J=16.0 Hz, α), 7.68-7.74 (2H, m, 2,6), 9.71 (1H, d, J=7.7 Hz, γ); $\delta_C$ 129.4 (2, 6), 129.5 (β), 129.9 (3, 5), 131.9 (4), 135.3 (1), 153.3 (α), 194.1 (γ). HR-MS (ESI) calcd for $C_9H_8O_2$ [(M−H)$^-$]: 147.0452; found: 147.0453.

Compound $12_G$.

NMR (500 MHz, acetone-$d_6$) δ 3.91 (3H, s, 3OMe), 6.65 (1H, dd, J=15.8, 7.8 Hz, β), 6.91 (1H, d, J=8.1 Hz, 5), 7.19 (1H, dd, J=8.2, 2.0 Hz, 6), 7.36 (1H, d, J=2.2 Hz, 2), 7.55 (1H, d, J=15.8 Hz, α), 8.38 (1H, s, 4OH), 9.62 (1H, d, J=7.8 Hz, γ); $\delta_C$ 56.3 (3OMe), 111.4 (2), 116.2 (5), 124.8 (6), 126.9 (β), 127.4 (1), 148.8 (3), 150.8 (4), 154.1 (α), 194.0 (γ). HR-MS (ESI) calcd for $C_{10}H_{10}O_3$ [(M−H)$^-$]: 177.0557; found: 177.0557.

Compound $12_S$.

$^1$H NMR (500 MHz, acetone-$d_6$) δ 3.88 (6H, s, OMe), 6.68 (1H, dd, J=15.8, 7.8 Hz, β), 7.06 (2H, s, 2, 6), 7.53 (1H, d, J=15.8 Hz, α), 8.00 (1H, s, OH), 9.62 (1H, d, J=7.8 Hz, γ). $^{13}$C NMR (126 MHz, acetone-$d_6$) δ 56.6 (OMe), 107.2 (2, 6), 126.1 (1), 127.2 (β), 140.1 (4), 148.9 (3, 5), 154.4 (α), 193.9 (γ). HR-MS (ESI) calcd for $C_{11}H_{12}O_4$ [(M−H)$^-$]: 207.0663; found: 207.0662.

Compound 13.

$^1$H NMR (500 MHz, acetone-$d_6$) δ 3.82 (6H, s, OMe), 5.05 (1H, dd, J=10.9, 1.0 Hz, β), 5.64 (1H, dd, J=17.6, 1.0 Hz, β), 6.62 (1H, dd, J=17.6, 10.9 Hz, α), 6.76 (2H, s, 2, 6), 7.32 (1H, s, 4OH). $^{13}$C NMR (126 MHz, acetone-$d_6$) δ 55.2 (OMe), 103.3 (2, 6), 110.0 (β), 128.0 (1), 135.7 (4), 136.7 (α), 147.4 (3, 5). HR-MS (ESI) calcd for $C_{10}H_{12}O_3$ [(M−H)$^-$]: 179.0714; found: 179.0715.

Compound 14 (cis).

$^1$H NMR (500 MHz, acetone-$d_6$) δ 3.82 (6H, s, 3OMe, 3'OMe), 5.8 (1H, d, J=7.0 Hz, α), 6.28 (1H, d, J=7.04, β), 6.62 (1H, m, 6'), 6.69-6.77 (3H, m, 5, 1', 2'), 7.08-7.14 (2H, m, 6, 5'), 7.50 (1H, s, 4OH), 7.56 (1H, d, J=1.74 Hz, 2). $^{13}$C NMR (126 MHz, acetone-$d_6$) δ 55.2 (3OMe, 3'OMe), 106.5 (1', 6'), 107.1 (α), 113.2 (2), 115.3 (2'), 119.1 (5), 122.2 (6), 125.8 (5'), 128.1 (1), 136.6 (4'), 145.8 (4), 146.2 (β), 147.9 (3), 153.7 (3'). HR-MS (ESI) calcd for $C_{16}H_{15}O_4$ [(M−H)$^-$]: 271.0970; found: 271.0973.

Compound 14 (trans).

$^1$H NMR (500 MHz, acetone-$d_6$) δ 3.82 (6H, s, 3OMe, 3'OMe), 5.30 (1H, d, J=15.3 Hz, α), 6.62 (1H, m, 6'), 6.69-6.77 (3H, m, 5, 1', 2'), 7.03 (1H, d, J=15.3 Hz, 13) 7.08-7.14 (2H, m, 6, 5'), 7.50 (1H, s, 4OH), 7.56 (1H, d, J=1.74 Hz, 2). $^{13}$C NMR (126 MHz, acetone-$d_6$) δ 55.2 (3OMe, 3'OMe), 106.5 (1', 6'), 107.1 (α), 113.2 (2), 115.3 (2'), 119.1 (5), 122.2 (6), 125.8 (5'), 128.1 (1), 136.6 (4'), 145.8 (4), 146.2 (β), 147.9 (3), 153.7 (3'). HR-MS (ESI) calcd for $C_{16}H_{15}O_4$ [(M−H)$^-$]: 271.0970; found: 271.0973.

Compound $15_G$.

$^1$H NMR (500 MHz, acetone-$d_6$) δ 3.87 (3H, s, 3'OMe), 3.91 (3H, s, 3OMe), 4.53 (1H, d, J=2.3 Hz, γ), 5.05 (1H, d, J=2.3 Hz, γ), 6.93 (1H, d, J=8.3 Hz, 5), 6.96 (1H, dd, J=8.0, 7.3, 1.6 Hz, 6'), 7.09 (1H, dd, J=7.9, 1.6 Hz, 5'), 7.14 (dd, J=8.2, 1.6 Hz, 1H, 2'), 7.19 (ddd, J=8.3, 7.3, 1.6 Hz, 1H, 1'), 7.68 (d, J=2.0 Hz, 1H, 2), 7.75 (dd, J=8.3, 2.0 Hz, 1H, 6), 8.60 (s, 1H, 4OH). $^{13}$C NMR (126 MHz, acetone-$d_6$) δ 56.1 (3'OMe), 56.2 (3OMe), 97.9 (γ), 113.5 (2), 114.0 (2'), 115.3 (5), 121.9 (6'), 122.5 (5'), 126.0 (6), 126.8 (1'), 129.0 (1), 143.9 (4'), 148.0 (3), 152.1 (3'), 152.6 (4), 159.4 (β), 188.8 (α). HR-MS (ESI) calcd for $C_{17}H_{16}O_5$ [(M−H)$^-$]: 299.0925; found: 299.0926.

Compound $15_{G''}$.

$^1$H NMR (500 MHz, acetone-$d_6$) δ 3.87 (3H, s, 3OMe), 3.88 (3H, s, 3'OMe), 3.90 (3H, s, 4OMe), 4.54 (1H, d, J=2.3 Hz, γ), 5.07 (1H, d, J=2.3 Hz, γ), 6.97 (1H, td, J=8.6, 7.6, 1.5 Hz, 6'), 7.07 (1H, d, J=8.4 Hz, 5), 7.10 (1H, dd, J=7.9, 1.6 Hz, 5'), 7.14 (1H, dd, J=8.2, 1.6 Hz, 2'), 7.19 (1H, ddd, J=8.4, 7.6, 1.5 Hz, 1'), 7.63 (1H, d, J=2.0 Hz, 2), 7.82 (1H, dd, J=8.5, 2.0 Hz, 6). $^{13}$C NMR (126 MHz, acetone-$d_6$) δ 56.0 (OMe), 56.2 (OMe), 56.2 (OMe), 98.1 (γ), 111.3 (5), 113.1 (2), 114.0 (2'), 121.9 (6'), 122.5 (5'), 125.6 (6), 126.8 (1'), 129.7 (1), 143.8 (4'), 149.8 (3), 152.1 (3'), 154.7 (4), 159.4 (β), 189.0 (α). HR-MS (ESI) calcd for $C_{18}H_{18}O_5$ [(M+H)$^+$]: 315.1227; found: 315.1222.

Compound $16_{GG}$.

$^1$H NMR (500 MHz, acetone-$d_6$) δ 3.71 (3H, s, 3OMe), 3.91 (3H, s, 3'OMe), 6.71 (1H, dd, J=8.1, 1.5 Hz, 5'), 6.78 (1H, td, J=7.7, 1.4 Hz, 6'), 6.81 (1H, d, J=8.3 Hz, 5), 6.98 (1H, ddd, J=8.2, 7.4, 1.5 Hz, 1'), 7.06 (1H, dd, J=8.2, 1.4 Hz, 2'), 7.22 (1H, s, α), 7.25 (1H, dd, J=8.3, 2.0 Hz, 6), 7.54 (1H, d, J=2.0 Hz, 2), 9.43 (1H, s, γ). $^{13}$C NMR (126 MHz, acetone-$d_6$) δ 56.1 (3OMe), 56.6 (3'OMe), 114.0 (2'), 114.2 (2), 115.2 (5'), 116.4 (5), 122.0 (6'), 124.0 (1'), 125.8 (1), 127.4 (6), 139.7 (α), 146.6 (4'), 148.4 (β), 149.0 (3), 150.3 (3'), 151.1 (4), 189.5 (γ). HR-MS (ESI) calcd for $C_{17}H_{16}O_5$ [(M−H)$^-$]: 299.0925; found: 299.0925.

Compound $16_{SG}$.

$^1$H NMR (500 MHz, acetone-$d_6$) δ 3.75 (6H, s, 3OMe, 5OMe), 3.89 (3H, s, 3'OMe), 6.71 (1H, dd, J=8.0, 1.6 Hz, 5'), 6.78 (1H, td, J=7.7, 1.4 Hz, 6'), 6.98 (1H, ddd, J=8.2, 7.4, 1.5 Hz, 1'), 7.06 (1H, dd, J=8.2, 1.4 Hz, 2'), 7.24 (1H, s, 2, 6), 7.26 (1H, s, α), 7.98 (1H, s, OH), 9.51 (1H, s, γ). $^{13}$C NMR (126 MHz, acetone-$d_6$) δ 56.2 (3'OMe), 56.4 (3OMe, 5OMe), 109.4 (2), 113.5 (2'), 114.6 (5'), 121.4 (6'), 123.3 (1'), 124.1 (1), 138.2 (α), 139.8 (4), 146.2 (4'), 148.2 (β), 148.7 (3), 149.9 (3'), 187.9 (γ). HR-MS (ESI) calcd for $C_{18}H_{18}O_6$ [(M−H)$^-$]: 329.1031; found: 329.1030.

Compound $17_{G''}$.

$^1$H NMR (500 MHz, acetone-$d_6$) δ 3.78 (3H, s, 3'OMe), 3.84 (3H, s, 3OMe), 3.88 (3H, s, 4OMe), 4.04 (2H, dd, J=7.0, 5.2 Hz, γ), 4.26 (1H, t, J=6.3 Hz, 9OH), 5.53 (1H, t, J=5.1 Hz, 3), 6.77 (1H, ddd, J=8.2, 7.5, 1.6 Hz, 6'), 6.85 (1H, dd, J=8.1, 1.6 Hz, 5'), 6.89 (1H, td, J=7.7, 1.6 Hz, 1'), 6.96 (1H, dd, J=8.1, 1.6 Hz, 2'), 7.04 (1H, d, J=8.5 Hz, 5), 7.64 (1H, d, J=2.1 Hz, 2), 7.83 (1H, dd, J=8.5, 2.1 Hz, 6). $^{13}$C NMR (126 MHz, acetone-$d_6$) δ 56.0 (3OMe), 56.1 (3'OMe), 56.2 (4OMe), 64.0, 64.1 (γ), 83.7, 83.7 (β), 111.4 (5), 112.0 (2), 113.6 (2'), 116.7 (5'), 121.5 (6'), 123.0 (1'), 124.3 (6), 129.4 (1), 148.4 (4'), 150.0 (3), 151.0 (3'), 154.9 (4), 195.9 (α). HR-MS (ESI) calcd for $C_{18}H_{20}O_6$ [(M+H)$^+$]: 333.1333; found: 333.1326.

Compound $17_{S''}$.

$^1$H NMR (500 MHz, acetone-$d_6$) δ 3.73 (6H, s, 5'OMe, 3'OMe), 3.80 (3H, s, 4OMe), 3.80-3.94 (3H, m, γ, 9OH), 3.86 (6H, s, 5OMe, 3OMe), 5.16-5.27 (1H, m, 3), 6.68 (2H, d, J=8.4 Hz, 2', 6'), 7.02 (1H, t, J=8.4 Hz, 1'), 7.43 (2H, s, 6, 2). $^{13}$C NMR (126 MHz, acetone-$d_6$) δ 55.0 (5'OMe, 3'OMe), 55.2 (5OMe, 3OMe), 59.3 (4OMe), 62.1 (γ), 84.9 (β), 104.9 (2', 6'), 105.9 (6, 2), 123.5 (1'), 130.9 (1), 135.8 (4'), 142.1 (4), 152.5 (3', 5'), 152.7 (5, 3), 194.6 (α). HR-MS (ESI) calcd for $C_{21}H_{26}O_8$ [(M+H)$^+$]: 407.1700; found: 407.1690.

Compound 19.

$^1$H NMR (500 MHz, acetone-d$_6$) δ 3.62 (1H, q, J=6.2 Hz, β), 3.82 (3H, s, 3OMe), 3.85-3.96 (2H, m, 9), 3.92 (3H, s, 3'OMe), 4.31 (1H, t, J=6.6, 5.4 Hz, 9OH), 5.66 (1H, d, J=6.7 Hz, α), 6.68 (1H, dd, J=15.8, 7.8 Hz, 13'), 6.82 (1H, d, J=8.1 Hz, 5), 6.89 (1H, dd, J=8.0, 1.7 Hz, 6), 7.05 (1H, d, J=2.0 Hz, 2), 7.32 (2H, dd, J=7.7, 1.4 Hz, 2', 6'), 7.61 (1H, d, J=15.8 Hz, α'), 7.81 (1H, s, 4OH), 9.64 (1H, d, J=7.8 Hz, γ'). $^{13}$C NMR (126 MHz, acetone-d$_6$) δ 54.2 (β), 56.2 (3OMe), 56.3 (3'OMe), 64.2 (9), 89.4 (α), 110.5 (2), 113.3, 113.3 (2'), 115.7 (5), 119.6 (6'), 119.7 (6), 127.0 (β'), 128.9 (1'), 131.1 (4'), 133.6 (1), 145.6 (3'), 147.4, 147.5 (4), 148.4 (3), 152.3 (5'), 154.3 (α'), 154.3, 193.9 (γ'). HR-MS (ESI) calcd for C$_{20}$H$_{20}$O$_6$ [(M–H)$^-$]: 355.1187; found: 355.1189.

What is claimed is:

1. A method of selectively reacting lignin or a lignin-derived reactant to yield an aromatic product, the method comprising:
reacting lignin or a lignin-derived reactant with a molybdenum-containing catalyst selected from the group consisting of MoO$_3$, Na$_2$MoO$_4$.2H$_2$O, MoO$_2$Cl$_2$, [C$_5$H$_5$Mo(CO)$_3$]$_2$, and Mo(dppf)(CO)$_4$, in a solvent, for a time and at a temperature wherein at least a portion of the lignin or lignin-derived reactant is selectively converted into an aromatic product.

2. The method of claim 1, wherein the lignin or a lignin-derived reactant is reacted at a temperature of from 120° C. to 250° C.

3. The method of claim 1, wherein the lignin or a lignin-derived reactant is reacted at a temperature of from 120° C. to 200° C.

4. The method of claim 1, wherein the lignin or a lignin-derived reactant is reacted at a temperature of from 120° C. to 160° C.

5. The method of claim 1, in which the temperature is established by microwave irradiation.

6. The method of claim 1, in which the temperature is established by radiant heating.

7. The method of claim 1, wherein the solvent is selected from the group consisting of dimethyl sulfoxide (DMSO), gamma-valerolactone (GVL), dimethylformamide (DMF), and cyclohexanone.

8. The method of claim 1, wherein the solvent is DMSO, and the lignin or a lignin-derived reactant is reacted with the molybdenum-containing catalyst in the absence of any additional oxidizing agents.

9. The method of claim 1, wherein the solvent is not DMSO, and the lignin or a lignin-derived reactant is reacted with the molybdenum-containing catalyst in the presence of an additional oxidizing agent.

10. The method of claim 9, wherein the lignin or a lignin-derived reactant is reacted with the molybdenum-containing catalyst in the presence of an additional oxidizing agent selected from the group consisting of DMSO, O$_2$, hydrogen peroxide, benzoyl peroxide, and ammonium persulfate.

11. A method of selectively reacting lignin or a lignin-derived reactant to yield an aromatic product, the method comprising:
reacting lignin or a lignin-derived reactant with a molybdenum-containing catalyst, in a solvent, for a time and at a temperature wherein at least a portion of the lignin or lignin-derived reactant is selectively converted into an aromatic product;
wherein the aromatic product comprises sinapaldehyde.

12. A method of selectively reacting lignin or a lignin-derived reactant to yield an aromatic product, the method comprising:
reacting lignin or a lignin-derived reactant with a molybdenum-containing catalyst selected from the group consisting of MoO$_3$, Na$_2$MoO$_4$.2H$_2$O, MoO$_2$Cl$_2$, [C$_5$H$_5$Mo(CO)$_3$]$_2$, and Mo(dppf)(CO)$_4$, in a solvent, in the presence of an additional oxidizing agent, for a time and at a temperature wherein at least a portion of the lignin or lignin-derived reactant is selectively converted into an aromatic product.

13. The method of claim 12, wherein the lignin or a lignin-derived reactant is reacted at a temperature of from 120° C. to 250° C.

14. The method of claim 12, wherein the lignin or a lignin-derived reactant is reacted at a temperature of from 120° C. to 200° C.

15. The method of claim 12, wherein the lignin or a lignin-derived reactant is reacted at a temperature of from 120° C. to 160° C.

16. The method of claim 12, in which the temperature is established by microwave irradiation.

17. The method of claim 12, in which the temperature is established by radiant heating.

18. The method of claim 12, wherein the solvent is selected from the group consisting of dimethyl sulfoxide (DMSO), gamma-valerolactone (GVL), dimethylformamide (DMF), and cyclohexanone.

19. The method of claim 1, wherein the solvent is not DMSO.

20. The method of claim 19, wherein the lignin or a lignin-derived reactant is reacted with the molybdenum-containing catalyst in the presence of an additional oxidizing agent, and wherein the additional oxidizing agent is selected from the group consisting of DMSO, O$_2$, hydrogen peroxide, benzoyl peroxide, and ammonium persulfate.

21. The method of claim 12, wherein the additional oxidizing agent is selected from the group consisting of DMSO, O$_2$, hydrogen peroxide, benzoyl peroxide, and ammonium persulfate.

22. A method of selectively reacting lignin or a lignin-derived reactant to yield an aromatic product, the method comprising:
reacting lignin or a lignin-derived reactant with a molybdenum-containing catalyst, in a solvent, in the presence of an additional oxidizing agent, for a time and at a temperature wherein at least a portion of the lignin or lignin-derived reactant is selectively converted into an aromatic product;
wherein the aromatic product comprises sinapaldehyde.

23. The method of claim 22, wherein the molybdenum-containing catalyst is selected from the group consisting of MoO$_2$Cl$_2$(DMSO)$_2$, MoO$_3$, Na$_2$MoO$_4$.2H$_2$O, MoO$_2$Cl$_2$, [C$_5$H$_5$Mo(CO)$_3$]$_2$, and Mo(dppf)(CO)$_4$.

24. The method of claim 22, wherein the lignin or a lignin-derived reactant is reacted at a temperature of from 120° C. to 250° C.

25. The method of claim 22, wherein the lignin or a lignin-derived reactant is reacted at a temperature of from 120° C. to 200° C.

26. The method of claim 22, wherein the lignin or a lignin-derived reactant is reacted at a temperature of from 120° C. to 160° C.

27. The method of claim 22, in which the temperature is established by microwave irradiation.

28. The method of claim 22, in which the temperature is established by radiant heating.

29. The method of claim 22, wherein the solvent is selected from the group consisting of dimethyl sulfoxide (DMSO), gamma-valerolactone (GVL), dimethylformamide (DMF), and cyclohexanone.

30. The method of claim 22, wherein the additional oxidizing agent is selected from the group consisting of DMSO, $O_2$, hydrogen peroxide, benzoyl peroxide, and ammonium persulfate.

31. The method of claim 11, wherein the molybdenum-containing catalyst is selected from the group consisting of $MoO_2Cl_2(DMSO)_2$, $MoO_3$, $Na_2MoO_4 \cdot 2H_2O$, $MoO_2Cl_2$, $[C_5H_5Mo(CO)_3]_2$, and $Mo(dppf)(CO)_4$.

32. The method of claim 11, wherein the lignin or a lignin-derived reactant is reacted at a temperature of from 120° C. to 250° C.

33. The method of claim 11, wherein the lignin or a lignin-derived reactant is reacted at a temperature of from 120° C. to 200° C.

34. The method of claim 11, wherein the lignin or a lignin-derived reactant is reacted at a temperature of from 120° C. to 160° C.

35. The method of claim 11, in which the temperature is established by microwave irradiation.

36. The method of claim 11, in which the temperature is established by radiant heating.

37. The method of claim 11, wherein the solvent is selected from the group consisting of dimethyl sulfoxide (DMSO), gamma-valerolactone (GVL), dimethylformamide (DMF), and cyclohexanone.

38. The method of claim 11, wherein the solvent is DMSO, and the lignin or a lignin-derived reactant is reacted with the molybdenum-containing catalyst in the absence of any additional oxidizing agents.

39. The method of claim 11, wherein the solvent is not DMSO, and the lignin or a lignin-derived reactant is reacted with the molybdenum-containing catalyst in the presence of an additional oxidizing agent.

40. The method of claim 39, wherein the lignin or a lignin-derived reactant is reacted with the molybdenum-containing catalyst in the presence of an additional oxidizing agent selected from the group consisting of DMSO, $O_2$, hydrogen peroxide, benzoyl peroxide, and ammonium persulfate.

41. The method of claim 11, wherein the solvent is not DMSO.

42. The method of claim 41, wherein the lignin or a lignin-derived reactant is reacted with the molybdenum-containing catalyst in the presence of an additional oxidizing agent, and wherein the additional oxidizing agent is selected from the group consisting of DMSO, $O_2$, hydrogen peroxide, benzoyl peroxide, and ammonium persulfate.

* * * * *